(12) United States Patent
Miller et al.

(10) Patent No.: US 7,250,145 B1
(45) Date of Patent: Jul. 31, 2007

(54) METHOD AND APPARATUS FOR STERILIZING MAIL AND TEXTILE ARTICLES

(75) Inventors: Jimmie D. Miller, 1304 N. 8th St., Arkansas City, KS (US) 67005; Blair Sutton, Lawrence, KS (US)

(73) Assignee: Jimmie D. Miller, Arkansas City, KS (US)

( * ) Notice: Subject to any disclaimer, the term of this patent is extended or adjusted under 35 U.S.C. 154(b) by 611 days.

(21) Appl. No.: 10/833,242

(22) Filed: Apr. 27, 2004

Related U.S. Application Data (63) Continuation-in-part of application No. 10/223,919, filed on Aug. 20, 2002, now Pat. No. 6,737,029.

(60) Provisional application No. 60/337,648, filed on Dec. 7, 2001.

(51) Int. Cl.
*A61L 2/14* (2006.01)

(52) U.S. Cl. .................. 422/300; 422/292; 422/186.07; 232/30

(58) Field of Classification Search ................ 422/292, 422/300, 186.07; 232/30; 382/101
See application file for complete search history.

(56) References Cited

U.S. PATENT DOCUMENTS

2002/0150500 A1* 10/2002 Carman et al. ................ 422/28
2003/0145664 A1* 8/2003 Schwarz et al. ......... 73/863.22

\* cited by examiner

*Primary Examiner*—Gladys J P Corcoran
*Assistant Examiner*—Sean E. Conley
(74) *Attorney, Agent, or Firm*—Dale J. Ream (57) ABSTRACT

An apparatus for sterilizing various articles includes a chamber defining an airtight space and an entrance and exit. A vacuum pump is coupled to the chamber for withdrawing air therefrom which reduces the chamber air pressure. An ozone generator is coupled to the chamber for introducing ozone at atmospheric pressure therein following air withdrawal. This causes efficient diffusing of the ozone into the article for sterilizing it against anthrax. The ozone is then withdrawn into an ozone filter having a non-consumable catalyst for converting the ozone back into oxygen. The apparatus may be implemented using single or multiple chambers. In multiple chamber embodiments, a conveyor extending through water chambers may be utilized for conveying textile articles while more traditional conveyors may be utilized for mail articles.

10 Claims, 6 Drawing Sheets

METHOD AND APPARATUS FOR STERILIZING MAIL AND TEXTILE ARTICLES

CROSS REFERENCE TO RELATED APPLICATIONS

This application claims the benefit of U.S. application Ser. No. 10/223,919 filed Aug. 20, 2002 now U.S. Pat. No. 6,737,029, entitled Method and Apparatus for Sterilizing Mail which claims the benefit of U.S. Application No. 60/337,648, filed Dec. 7, 2001, entitled Device To Sterilize Anthrax Spores Being Sent Through The Mail.

BACKGROUND OF THE INVENTION

This invention relates to decontamination and sterilization devices and, more particularly, to a method and apparatus for sterilizing articles of mail that may be tainted with anthrax or other pathogens.

A single letter contaminated with anthrax or similar pathogens can cause serious health issues or even death to humans. In fact, a single letter may include thousands of times more than the lethal dose of anthrax. The threat of safety relative to the delivery of mail was accented by the anthrax infections following the historic terrorist attacks against the United States on Sep. 11, 2001. Several people were infected with anthrax as a result of letters containing the deadly pathogens. Postal offices and other businesses had to be shut down and fully sterilized. Anthrax in a single letter can cross-contaminate other articles of mail, postal sorting equipment, and the like. This is a significant problem in view of the 680 million pieces of mail handled by the U.S. Postal Service every day.

Various devices have been proposed for sterilizing medical equipment and other articles. Although assumably effective for their intended purposes, the existing devices are not suitable for sterilizing mail at the initial point of mail deposit or without damaging the mail. More particularly, the use of steam heat or intense dry heat would irreversibly damage mail. Further, chemical sterilization with ethylene oxide gas avoids the damages associated with heat sterilization but requires long cycle times and the handling of harsh chemicals. These disadvantages would be unacceptable for use in mass mail processing. Sterilization with gamma radiation, while effective, would be prohibitively expensive for use in the decentralized mail processing and delivery industry.

Therefore, it is desirable to have a method and apparatus for sterilizing mail quickly and without damaging the mail. Further, it is desirable to have a method and apparatus for sterilizing mail without generating excessive heat or pollution. In addition, it is desirable to have a method and apparatus for sterilizing mail that may be used in the mail sorting process.

SUMMARY OF THE INVENTION

A method and apparatus for sterilizing mail according to the present invention includes a chamber defining an airtight enclosed space and having an entrance and exit through which mail may be conveyed. A vacuum pump is coupled to the chamber for withdrawing air from the chamber and an article of mail therein. This withdrawal of air reduces the air pressure in the chamber. An ozone gas generator is also coupled to the chamber and is capable of introducing ozone therein after all gases have been removed by the vacuum pump. Introducing ozone into the low pressure environment causes the ozone to permeate the article of mail very quickly as the ozone seeks to diffuse in even concentration throughout the chamber. Ozone is an unstable molecule that reacts with organic matter such as bacteria and viruses. This reaction destroys critical components of organisms, thereby being an effective sterilizing agent against anthrax within an article of mail. The highly reactive property of ozone makes sterilization very quick compared to other disinfectant methodologies. Following sterilization, the ozone is withdrawn from the chamber by another operation of the vacuum pump or with another fan such that the ozone is collected in an ozone filter. The filter includes a non-consumable catalyst such as manganese dioxide which converts the ozone into oxygen. The apparatus may be implemented using a single chamber or using multiple chambers connected by airlocks (multi-stage implementation).

Therefore, a general object of this invention is to provide a method and apparatus for sterilizing mail from anthrax or other pathogenic poisoning.

Another object of this invention is to provide a method and apparatus, as aforesaid, which sterilizes articles of mail quickly and without exposure of persons to harsh or harmful chemicals.

Still another object of this invention is to provide a method and apparatus, as aforesaid, which sterilizes articles of mail without damaging the articles of mail.

Yet another object of this invention is to provide a method and apparatus, as aforesaid, which sterilizes mail without generating excessive heat or pollution.

A further object of this invention is to provide a method and apparatus, as aforesaid, which may be integrated into a conventional mail sorting process.

A still further object of this invention is to provide a sterilizing apparatus having a unique conveyor system for moving textile articles between multiple water and sterilizing chambers.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

A method and apparatus for sterilizing mail against anthrax and other pathogens will now be described in detail with reference to FIGS. 1 through 4 of the accompanying drawings.

Figure 1:
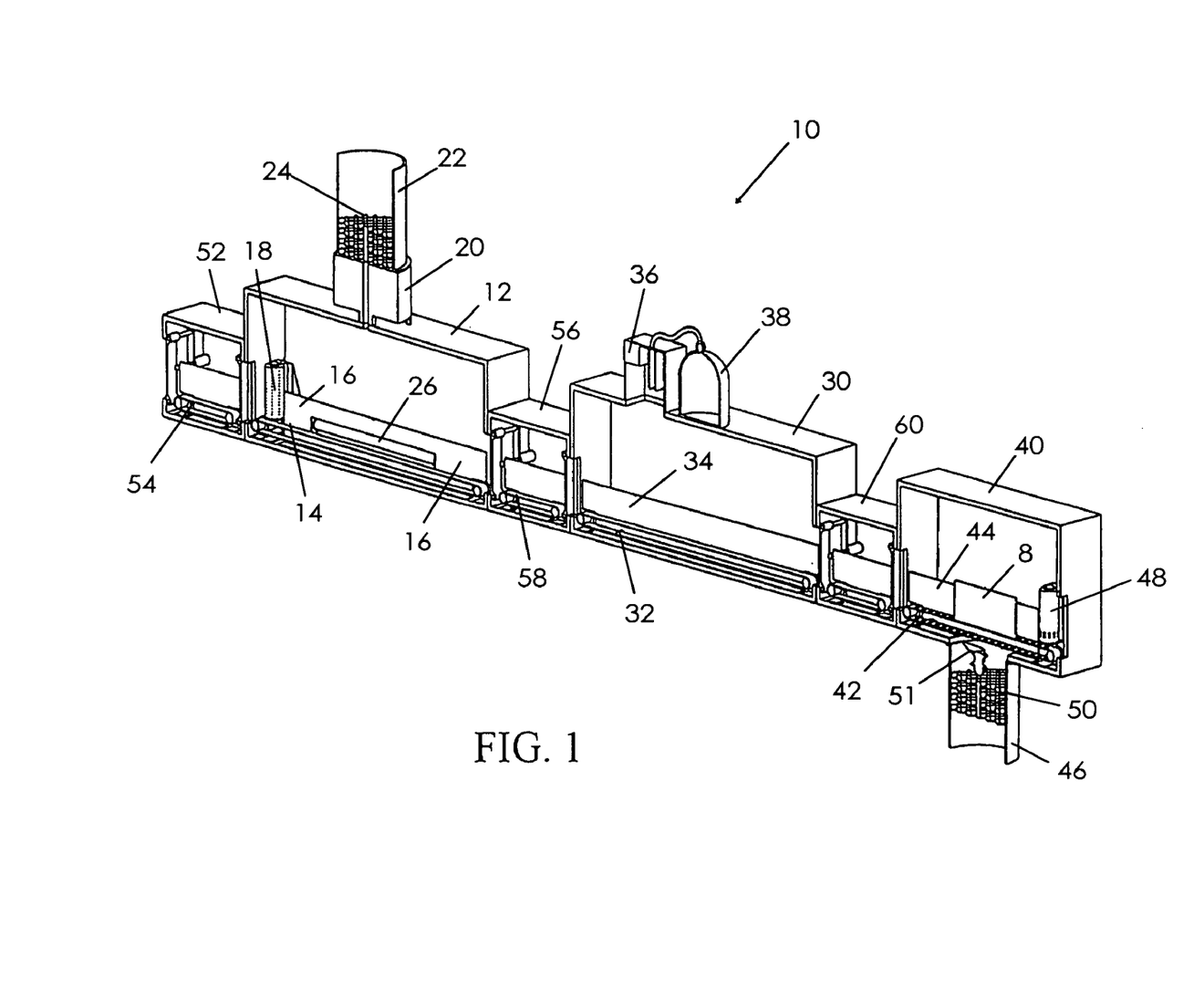
FIG. 1 is a perspective view, partially broken away, of a mail sterilization apparatus according to one embodiment of the present invention.
Figure 2:
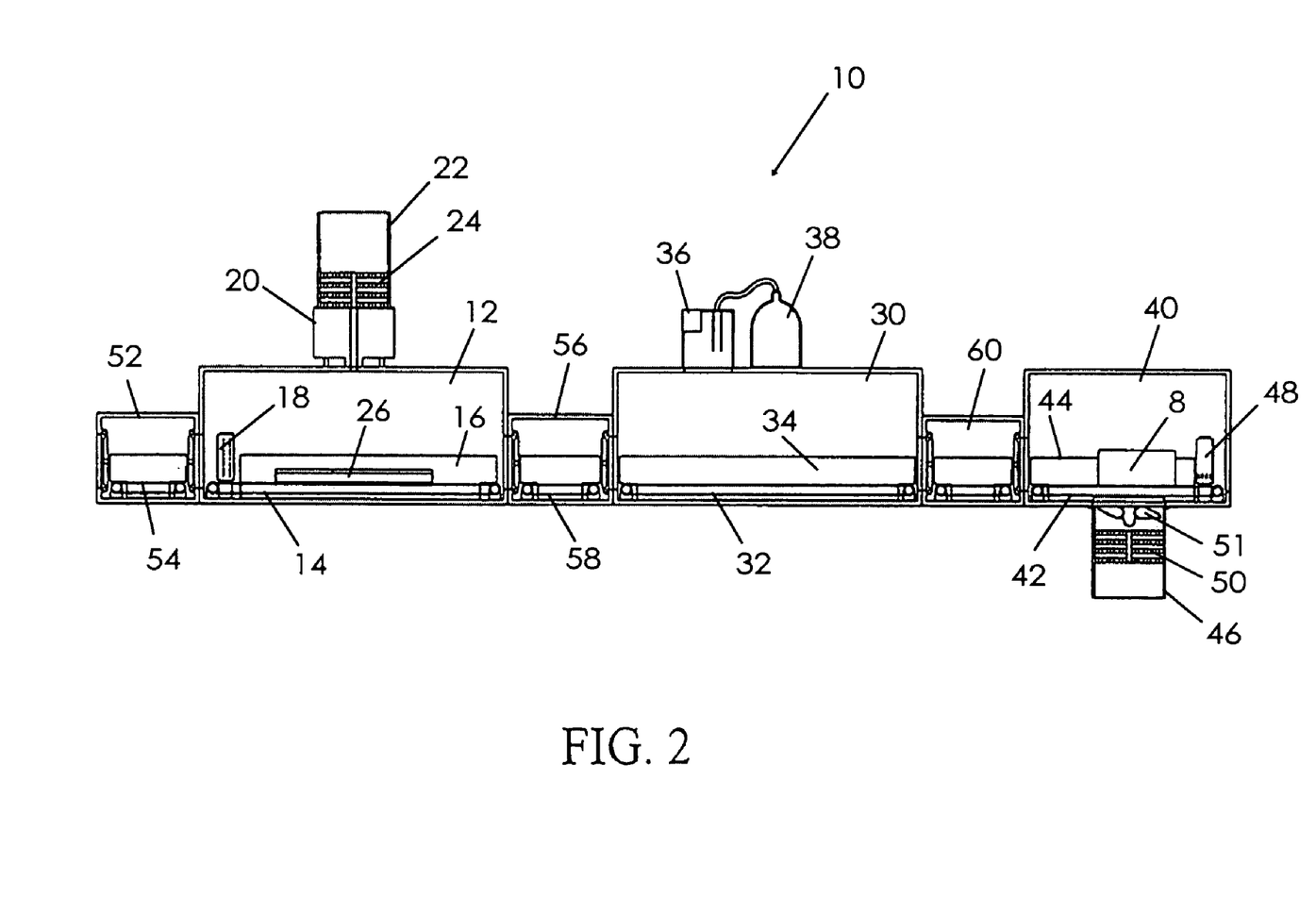
FIG. 2 is a side view of the mail sterilization apparatus as in FIG. 1.

A mail sterilizing apparatus 10 according to one embodiment of the present invention includes a multi-stage, multiple chamber construction (FIGS. 1 and 2). More particularly, the apparatus 10 includes a first chamber 12 having a rectangular or box-shaped configuration defining an enclosed interior space. The first chamber 12 may also be referred to as the vacuum chamber. The first chamber 12 includes entrance and exit openings at opposed ends thereof for entry and exit of articles of mail 8, respectively. A first conveyor 14 is positioned in the first chamber 12 and extends between the first chamber entrance and exit for moving an article of mail through the interior of the first chamber 12 along a first conveyance path. A first letter guide 16 extends along each side of the first conveyor 14 and is situated in an upstanding configuration for guiding an article of mail 8 along a first conveyance path defined by the first conveyor 14.

A first airlock 52 is coupled to the first chamber 12 adjacent the entrance thereto, the first airlock having doors that are selectively movable so as to seal or expose the entrance. A second airlock 56 is coupled to the first chamber 12 adjacent the exit therefrom, the second airlock 56 having doors that are selectively movable so as to seal or expose the exit. Of course, doors attached directly to the first chamber 12 for sealing or exposing the entrance and exit would also be a suitable construction. It is also understood that rotary airlocks would also be suitable rather than the two door airlocks shown. Therefore, the first chamber 12 is airtight when the first chamber entrance and exit are sealed. This is important as the air pressure within the first chamber 12 is modified as to be described in detail below. Each airlock 52, 56 further includes respective auxiliary conveyors 54, 58, respectively, for conveying an article of mail 8 therealong.

Preferably, a pair of perforation rollers 18 are mounted in upstanding configurations on opposed sides of the first chamber conveyor 14 adjacent the first chamber entrance, although a single perforation roller would be adequate. Thus, the perforation rollers 18 are positioned to bear against an article of mail 8 as it enters the first chamber 12. The perforation rollers 18 may be spring loaded so as to press against the article of mail 8 while accommodating various sizes of mail articles. Each perforation roller 18 includes a plurality of miniature pins or spikes for making almost imperceptible perforations in the article of mail 8 (i.e. in the envelope).

A vacuum pump 20 is coupled to the first chamber 12 and is in communication with the enclosed interior space thereof (FIGS. 1 and 2). An operation of the vacuum pump 20 withdraws air from the first chamber 12 and, more particularly, from the article of mail 8 being conveyed therethrough. The perforations placed in the article of mail 8 make this air withdrawal faster and more complete.

A first ozone filter 22 is connected to the vacuum pump 20 for receiving all air withdrawn from the first chamber 12 (FIG. 1). Preferably, the first ozone filter 22 includes a non-consumable catalyst 24 of manganese dioxide for converting any withdrawn ozone into oxygen before the air is exhausted into the environment surrounding the apparatus 10. Manganese dioxide is the preferred catalyst in that it is not consumed by reaction with ozone, decomposes ozone at ambient temperature, and decomposes ozone quickly.

One or more ultraviolet lamps 26 may be positioned within the first chamber 12. Ultraviolet light is a form of non-ionized radiation that is effective to irradiate and destroy pathogens upon exposure. Thus, exposing articles of mail to ultraviolet light sterilizes the outer surfaces thereof but does not penetrate envelopes or other packaging. However, sterilizing the outer surfaces of mail articles is still advantageous so as to prevent cross-contamination of the apparatus 10 itself or of postal workers.

The apparatus 10 includes a second chamber 30 connected to the first chamber 12 (FIG. 1). The second chamber 30 includes a construction substantially similar to the construction of the first chamber 12, including defining an entrance and exit. The second chamber 30 further includes a second conveyor 32 extending between the second chamber entrance and exit for moving an article of mail therethrough and includes second mail guides 34. More particularly, the second airlock 56 links the first and second chambers together. The second airlock 56 enables the article of mail 8 from which air has been withdrawn to maintain its low pressure as it exits the first chamber 12 and enters the second chamber 30. A third airlock 60 having a construction substantially similar to the airlocks previously described is coupled to the second chamber 30 adjacent the second chamber exit for selectively sealing the exit and making the second chamber airtight.

An ozone generator 36 is coupled to the second chamber 30 and is in communication with the enclosed interior space thereof. The ozone generator 36 is operatively connected to an oxygen tank 38 as its source of oxygen for ozone gas generation. Although the ozone generator 36 is capable of producing ozone using atmospheric air, a direct supply of oxygen can increase ozone concentration generation by over 400%. Once the article of mail 8 is received into the second chamber 30 and the second chamber 30 is sealed, the ozone generator 36 introduces a quantity of ozone gas into the second chamber 30. Of course, the second chamber 30 may already be filled with ozone when the article of mail 8 enters. The pressure differential between the article of mail 8 and the second chamber 30 causes the ozone to quickly diffuse and permeate the article of mail 8 and sterilize any microorganisms such as anthrax. Ozone is a powerful oxidant formed of three oxygen atoms ($O_3$). An ozone molecule is highly unstable and reacts with any organic matter including bacteria and viruses. Such a reaction is capable of splitting proteins and carbohydrates to damage critical components of organisms.

The apparatus 10 further includes a third chamber 40 connected to the second chamber 30 via the third airlock 60 (FIG. 1). The third chamber 40, which may also be referred to as the polishing chamber, includes a construction substantially similar to the construction of the chambers previously described, including having a third conveyor 42 and third mail guide 44. The third chamber 40 also defines a corresponding entrance and exit. In addition, a second ozone filter 46 is connected to the third chamber 40 for collecting ozone molecules remaining on the article of mail 8. The second ozone filter 46 includes a non-consumable catalyst 50 such as manganese dioxide for decomposing collected ozone into oxygen before exhausting it into the surrounding environment. A fan 51 is positioned within the third chamber 40 at the base of the second ozone filter 46 for drawing air from the third chamber 40 into the second ozone filter 46 (FIG. 2). It should be observed that the third conveyor 42 is perforated to allow air to be drawn more easily into the second ozone filter 46. It should be appreciated that air withdrawn from the first chamber 12 by the vacuum pump 20 may be funneled directly to the third chamber 40 such that only a single ozone filter would be needed.

At least one embossing roller 48 is mounted in the third chamber 40 adjacent the third chamber exit. The embossing roller 48 is positioned in an upstanding configuration adjacent a conveyance path defined by the third conveyor 42 such that articles of mail passing therealong will contact the embossing roller 48. The embossing roller 48 is suitable to leave a mark, impression, or indicia upon articles of mail with which it makes contact so as to indicate to mail recipients that the article of mail has completed the sterilization cycle. The article of mail 8 is then passed through the third chamber exit and may continue in a conventional mail sorting process, etc.

In use, the apparatus 10 may be configured as part of a flow-through mail sorting process or be used independently, e.g. in a corporate mailroom. A control panel (not shown) configured to properly sequence operations may be used to control the apparatus 10 if the operations are not otherwise sequenced into an existing mail sorting process. An article of mail 8 is inserted or directed into the entrance of the first chamber 12 where it is conveyed along the first conveyor 14. Of course, the article of mail 8 may start by passing through the first airlock 52 although that is not essential. The article of mail 8 is perforated by the perforation rollers 18 and then the vacuum pump 20 may operate to withdraw air from the first chamber 12. Either sequentially or simultaneously with the vacuum pump operation, the outer surfaces of the article of mail 8 may be exposed to ultraviolet light from the ultraviolet lamps 26.

The lowered pressure is maintained as the article of mail 8 is conveyed through the second airlock 56 and into the second chamber 30. Ozone at substantially atmospheric pressure may be introduced into the second chamber 30 and the pressure differential causes the ozone to quickly permeate the article of mail 8. The diffusion of ozone within the article of mail sterilizes any microorganisms contained therein, such as anthrax spores. It should be appreciated that the ozone would eventually diffuse evenly into the article of mail in the absence of a pressure differential or perforations, but the pressure differential and perforations speed the process significantly. The article of mail 8 may then be conveyed through the third airlock 60 into the third chamber 40 where remaining ozone is drawn into the second ozone filter 50. This is the polishing stage which may conclude by embossing the article of mail 8 to indicate that it has completed the sterilization process.

Figure 3:
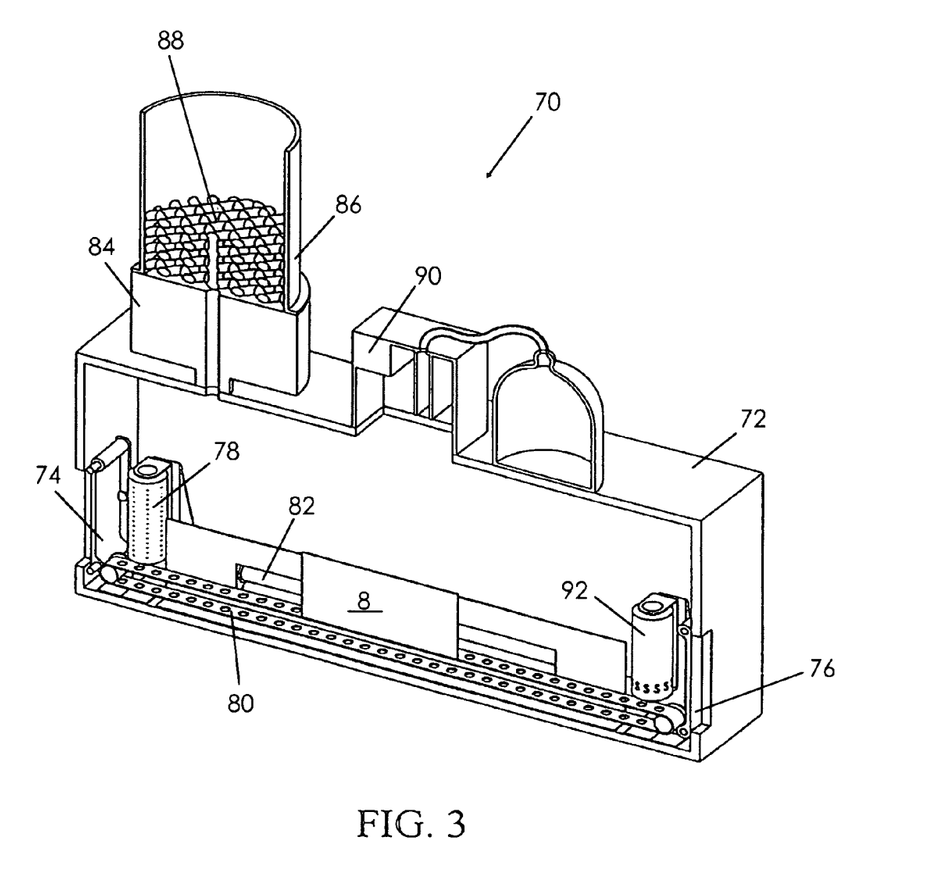
FIG. 3 is a perspective view of a mail sterilization apparatus, partially broken away, according to another embodiment of the present invention.
Figure 4:
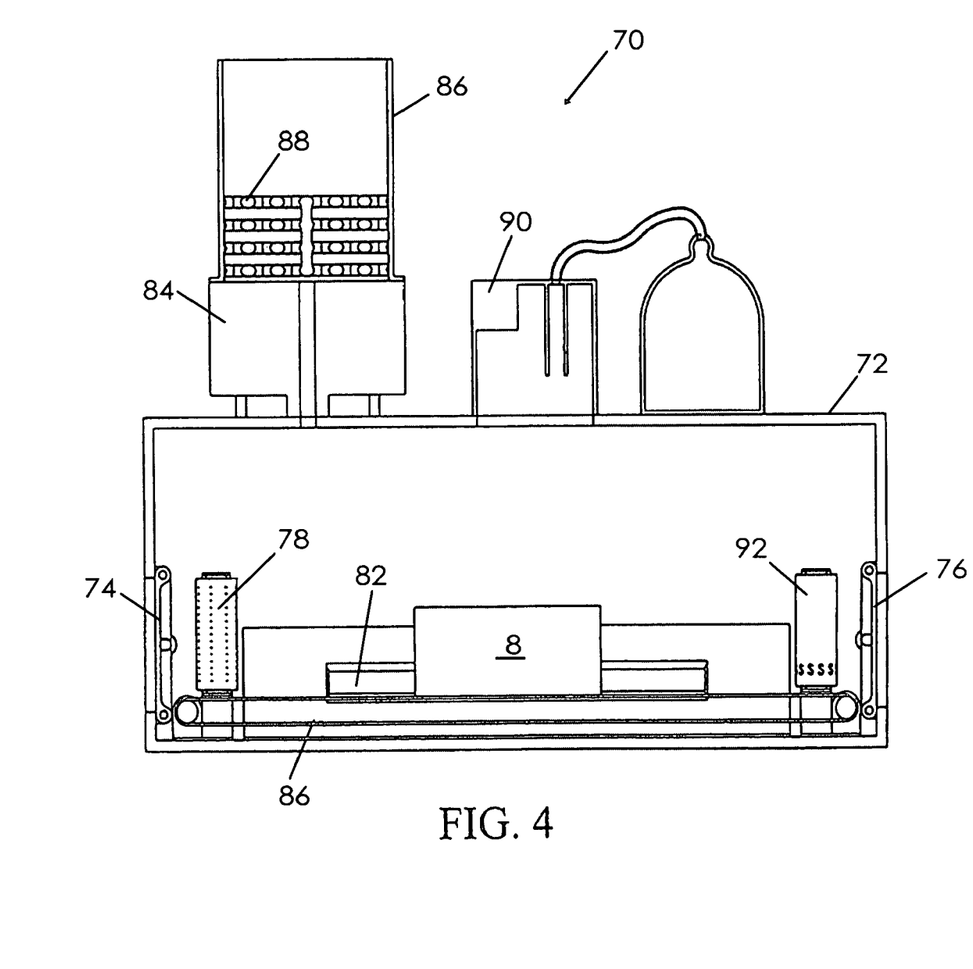
FIG. 4 is a side view of the mail sterilization apparatus as in FIG. 3.

A mail sterilization apparatus 70 according to another embodiment of the present invention is shown in FIGS. 3 and 4 and includes a construction substantially similar to the construction described above except as specifically noted below. The apparatus 70 according to this embodiment includes only a single chamber 72 but is capable of performing in a substantially similar manner as the apparatus first described. The single chamber 72 includes entrance 74 and exit 76 doors for sealing the entrance and exit openings as appropriate for the insertion or withdrawal of an article of mail 8. Perforation rollers 78 are mounted adjacent the entrance door 74 and along the path of a conveyor 80 for perforating the article of mail 8 as it is conveyed through the single chamber 72. One or more ultraviolet lamps 82 are positioned in the single chamber 72 along the path of the conveyor 80 for sterilizing the outer surfaces of an article of mail, in the manner described previously.

In the manner as described previously, a vacuum pump 84 is coupled to the single chamber 72 for withdrawing air from the single chamber 72 and from the article of mail 8. Withdrawn air is passed through an ozone filter 86 with a non-consumable catalyst 88 prior to being exhausted into the surrounding atmosphere. An ozone generator 90 is also coupled to the single chamber 72 for introducing ozone gas therein after operation of the vacuum pump 84. It is understood that the ozone is introduced at normal atmospheric pressure. Due to the pressure differential between the article of mail 8 and the ozone being introduced, the ozone quickly permeates the article of mail 8 for sterilizing any microorganisms therein. Following ozone sterilization, another operation of the vacuum pump 84 may evacuate the chamber of ozone before the article of mail 8 contacts an embossing roller 92 and exits the apparatus 70. This apparatus 70 is particularly convenient for use in a corporate mailroom, drop box, or residence.

In addition, it is contemplated that multiple tracks (e.g. conveyance paths) may be constructed within each chamber such that several articles of mail may be sterilized in parallel.

Figure 5:
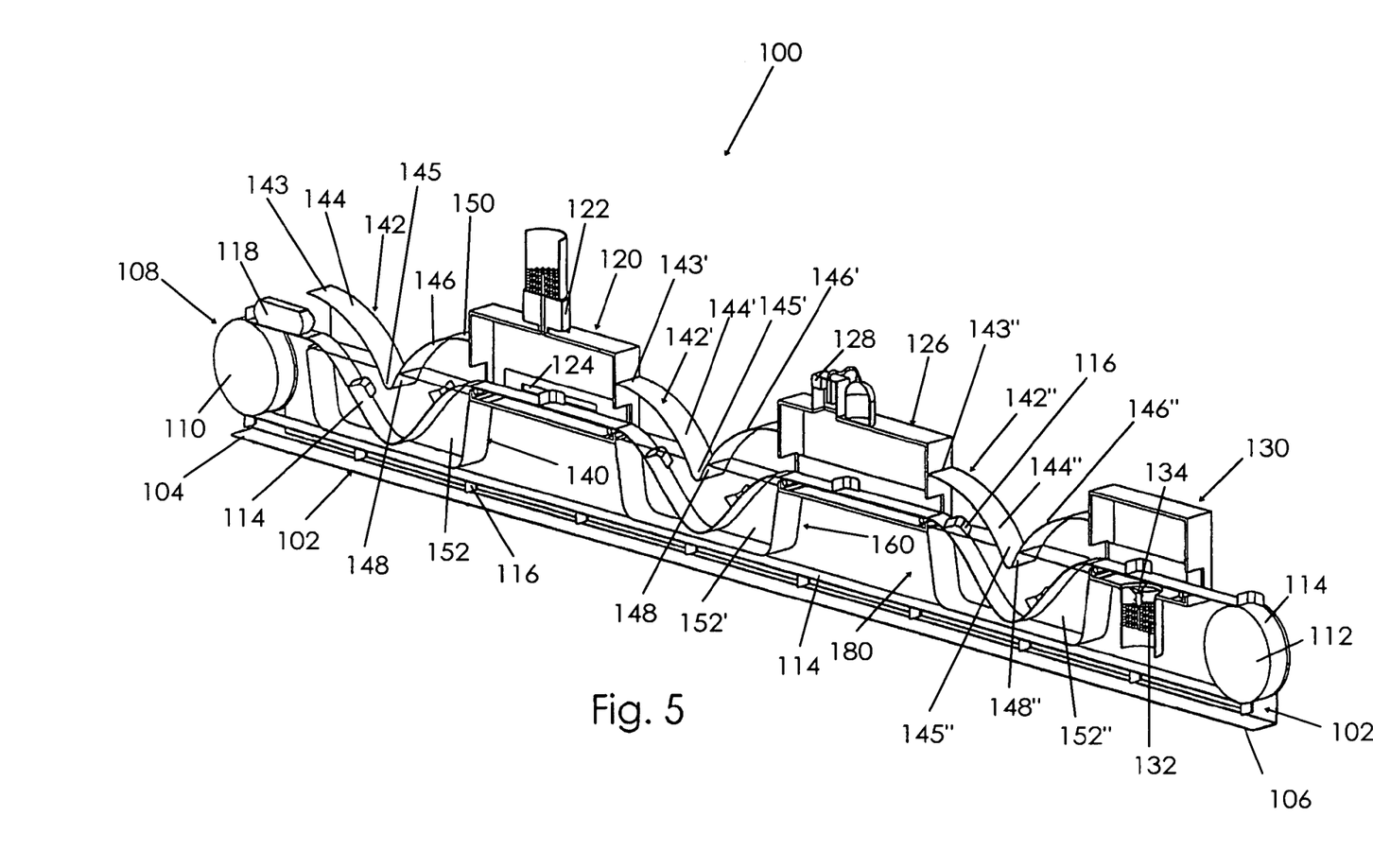
FIG. 5 is a perspective view, partially broken away, of a sterilization apparatus according to another embodiment of the present invention.
Figure 6:
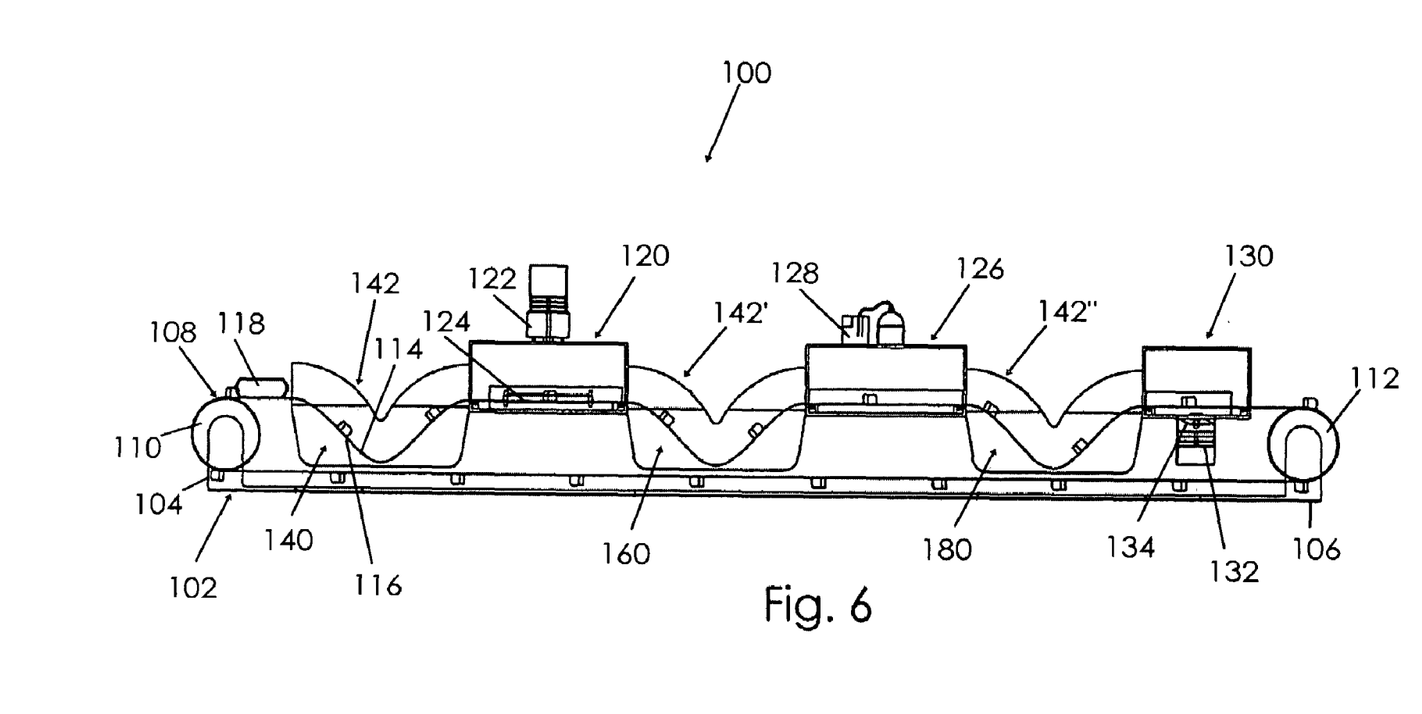
FIG. 6 is a side view of the sterilization apparatus as in FIG. 5.

A sterilizer apparatus 100 according to yet another embodiment of the present invention is shown in FIGS. 5 and 6. The sterilizer apparatus 100 according to this embodiment includes sterilization components substantially similar to those previously described. However, while this embodiment may be used to convey and sterilize articles of mail, this embodiment of the invention particularly includes unique structures developed for conveying textile articles 118 such as sheets, pillows, pillowcases and other textiles through the sterilizer components described previously.

More particularly, this embodiment of the sterilizer apparatus 100 includes a framework 102 as well as a conveyor assembly 108 that is uniquely directed toward conveying textiles through a multi-stage, multi-chamber construction. The conveyor assembly 108 includes first 110 and second 112 guide rollers pivotally coupled to upstream 104 and downstream 106 ends of the framework 102, respectively. The conveyor assembly 108 includes an elongate continuous conveyor belt 114 coupled about the guide rollers such that an operation of the guide rollers 110, 112 operates the conveyor in a downstream direction. A plurality of stop members 116 are mounted atop the conveyor belt 114 and spaced apart longitudinally therealong, each stop member 116 having a configuration for stabilizing and holding a textile article in place as the conveyor belt 114 moves through the sterilizing chambers described in more detail below.

This embodiment of the sterilizer apparatus 100 includes first 120, second 126, and third 130 sterilizing chambers having a construction substantially similar to the sterilizing chambers first described herein except as specifically noted below. Further, the sterilizer apparatus 100 includes first 140, second 160, and third 130 water chambers. The single conveyor assembly 108 extends through the water and sterilizing chambers and operates to convey an article 118 therethrough to be sterilized. Accordingly, a vacuum pump 122 is coupled to the first sterilizing chamber 120 for withdrawing air from the article 118 being conveyed through the first sterilizing chamber 120. Further, an ozone generator 128 is coupled to the second sterilizing chamber 126 for introducing ozone into the second sterilizing chamber 126 as the article 118 is moved therethrough. An ozone filter 132 is coupled to the third sterilizing chamber 130 and includes a non-consumable catalyst such as manganese dioxide. In addition, a fan 134 is mounted in the third sterilizing chamber 130 and is coupled to the ozone filter 132 for drawing air from the third sterilizing chamber 130 across the non-consumable catalyst and into the filter 132.

Each water chamber is configured for holding a respective quantity of water and defining a respective water level. While the sterilizing chambers define respective entrance and exit openings, they do not include movable airlock doors. Instead, the unique construction of the water chambers provides suitable airlock function, as described in detail below. With specific reference to FIG. 5, the first water chamber 140 includes an upper wall 142, which may also be referred to as a ceiling. The first water chamber upper wall 142 includes upstream 144 and downstream 146 portions connected to one another below the first water level that is defined within the first water chamber 140. As shown, the upstream portion 144 includes a first end 143 and a second end 145, the second end 145 being positioned below the first water level. The downstream portion 146 of the first water chamber upper wall 142 includes a first end 148 situated below the first water level and a second end 150 connected to the first sterilizing chamber 120 upwardly adjacent the first sterilizing chamber entrance.

The second 160 and third 180 water chambers include upper walls having substantially similar constructions which are referenced herein and on the drawings using identical numbers that are primed and double primed, respectively. It is understood that each water chamber include front and back 152 walls as can be seen in FIG. 5 so as to contain the water therein and to establish enclosed air spaces. The water chambers and sterilizing chambers are positioned in succession such that the article 118 to be sterilized is conveyed through a water chamber before entering the next sterilizing chamber. It should be appreciated that connection of upstream and downstream portions of respective water chamber upper walls establishes a closed airspace surrounding a respective sterilizing chamber.

In operation, the sterilizer apparatus 100 according to the embodiment shown in FIGS. 5 and 6 may be utilized as part of a traditional laundering process or used independently, i.e. as an independent article sterilizing process. An article 118 is placed upon the conveyor belt 114 and the conveyor assembly 108 is operated. Accordingly, the article 118 is moved beneath the water level of the first water chamber 140 and then into the first sterilizing chamber 120 where the air pressure is reduced by operation of the vacuum pump 122 and may be exposed to ultraviolet light by operation of the ultraviolet lamp 124. The reduced air pressure is maintained by the closed air spaces formed by the unique configurations of the water chamber upper walls.

The article 118 is further conveyed through the second water chamber 160 and then into the second sterilizing chamber 126 where the article is exposed to ozone upon operation of the ozone generator 128. The article may then be conveyed through the third water chamber 180 and finally into the third sterilizing chamber 130 where remaining ozone is drawn into the ozone filter 132 by operation of the fan 134. Use of hot air is anticipated in the third sterilizing chamber 130 so as to thoroughly dry the article as well.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. An apparatus for sterilizing an article, comprising:
a framework having opposed upstream and downstream ends;
a first water chamber mounted to said upstream end of said framework, said first water chamber configured for holding a first quantity of water and defining a first water level;
a conveyor extending through said first water chamber for conveying the article through said first quantity of water beneath said first water level;
a first sterilizing chamber mounted to said framework downstream from said first water chamber, said first sterilizing chamber defining an enclosed space and having a first entrance and a first exit above said first water level;
wherein said conveyor extends between said first entrance and said first exit for moving the article through said first sterilizing chamber enclosed space along a first conveyance path;
a vacuum pump coupled to said first sterilizing chamber for withdrawing air from the article being conveyed along said conveyor, said vacuum pump causing a reduced air pressure within said first sterilizing chamber;
a second water chamber mounted to said framework downstream from said first sterilizing chamber, said second water chamber configured to hold a second quantity of water and defining a second water level;
wherein said conveyor extends through said second water chamber for conveying the article through said second quantity of water below said second water level;
a second sterilizing chamber mounted to said framework downstream from said second water chamber, said second sterilizing chamber defining an enclosed space and having a second entrance and a second exit above said second water level;
wherein said conveyor extends between said second entrance and said second exit for moving the article through said second sterilizing chamber along a second conveyance path; and
an ozone generator coupled to said second sterilizing chamber for introducing ozone into said second sterilizing chamber as the article is moved therethrough.

2. The apparatus as in claim 1 further comprising an ultraviolet lamp positioned in said first sterilizing chamber along said first conveyance path for sterilizing outer surfaces of the article.

3. The apparatus as in claim 1 further comprising:
a third water chamber mounted to said framework downstream from said second sterilizing chamber, said third water chamber configured to hold a third quantity of water and defining a third water level;
wherein said conveyor extends through said third water chamber for conveying the article through said third quantity of water below said third water level;
a third sterilizing chamber mounted to said framework downstream from said third water chamber, said third sterilizing chamber defining an enclosed space and having a third entrance and a third exit above said third water level;
wherein said conveyor extends between said third entrance and said third exit for moving the article through said third sterilizing chamber along a third conveyance path; and
an ozone filter coupled to said third sterilizing chamber and having a non-consumable catalyst for converting ozone into oxygen.

4. The apparatus as in claim 1 wherein:
said first water chamber includes an upper wall having a first water chamber downstream portion, said first water chamber downstream portion having a first end positioned below said first water level and a second end connected to said first sterilizing chamber upwardly adjacent said first entrance;
said second water chamber includes an upper wall having a second water chamber upstream portion, said second water chamber upstream portion having a first end connected to said first sterilizing chamber upwardly adjacent said first exit; and whereby said first water chamber downstream portion and said second water chamber upstream portion form an airlock surrounding said first sterilizing chamber for retaining said reduced air pressure.

5. The apparatus as in claim 3 wherein:

said upper wall of said second water chamber includes a second water chamber downstream portion, said second water chamber downstream portion having a first end connected to said second end of said second water chamber upstream portion below said second water level and a second end connected to said second sterilizing chamber upwardly adjacent said second entrance;

said third water chamber includes an upper wall having a third water chamber upstream portion, said third water chamber upstream portion having a first end connected to said second sterilizing chamber upwardly adjacent said second exit and a second end positioned below said third water level; and whereby said second water chamber downstream portion and said third water chamber upstream portion form an airlock surrounding said second sterilizing chamber for preventing unintended release of ozone as the article is moved through said second sterilizing chamber.

6. The apparatus as in claim 3 further comprising:

a first guide roller pivotally coupled to said upstream end of said framework and coupled to said conveyor; and a second guide roller pivotally coupled to said downstream end of said framework and coupled to said conveyor, an operation of said first and second guide rollers moving said conveyor in a downstream direction.

7. The apparatus as in claim 6 wherein said conveyor includes a continuous conveyor belt.

8. The apparatus as in claim 7 wherein said conveyor includes a plurality of conveyor stop members mounted atop said conveyor belt and spaced apart longitudinally thereal­ong for stabilizing respective articles.

9. The apparatus as in claim 3 wherein said non-consum­able catalyst is manganese dioxide.

10. The apparatus as in claim 3 further comprising a fan mounted in said third sterilizing chamber and coupled to said ozone filter for drawing air from said third sterilizing chamber across said non-consumable catalyst and into said ozone filter.

* * * * *